United States Patent
Zucker et al.

(10) Patent No.: US 10,088,403 B2
(45) Date of Patent: Oct. 2, 2018

(54) METHOD AND DEVICE FOR DETERMINING SURFACE CHARACTERISTICS OF STENTS, AND STENT HAVING DEFINED SURFACE CHARACTERISTICS

(71) Applicants: Arik Zucker, Zürich (CH); Stefano Buzzi, Zürich (CH); Armin W. Mäder, Richterswil (CH); Vincent Milleret, Zürich (CH)

(72) Inventors: Arik Zucker, Zürich (CH); Stefano Buzzi, Zürich (CH); Armin W. Mäder, Richterswil (CH); Vincent Milleret, Zürich (CH)

(73) Assignee: QVANTEQ AG (CH)

( * ) Notice: Subject to any disclaimer, the term of this patent is extended or adjusted under 35 U.S.C. 154(b) by 515 days.

(21) Appl. No.: 14/371,719

(22) PCT Filed: Dec. 20, 2012

(86) PCT No.: PCT/EP2012/076426
§ 371 (c)(1),
(2) Date: Jul. 10, 2014

(87) PCT Pub. No.: WO2013/104512
PCT Pub. Date: Jul. 18, 2013

(65) Prior Publication Data
US 2015/0000430 A1 Jan. 1, 2015

(30) Foreign Application Priority Data
Jan. 11, 2012 (CH) ..................................... 0049/12

(51) Int. Cl.
*G01N 13/00* (2006.01)
*G01N 13/02* (2006.01)
(Continued)

(52) U.S. Cl.
CPC .......... *G01N 13/00* (2013.01); *A61F 2/0077* (2013.01); *A61F 2/89* (2013.01); *A61F 2/95* (2013.01);
(Continued)

(58) Field of Classification Search
CPC .......... G01N 13/00; G01N 13/02; A61F 2/98; A61F 2/89
See application file for complete search history.

(56) References Cited

U.S. PATENT DOCUMENTS 5,449,372 A 9/1995 Schmaltz et al.
6,119,511 A 9/2000 Christian et al.
(Continued)

FOREIGN PATENT DOCUMENTS

| | | |
|---|---|---|
| CN | 2 531 384 | 1/2003 |
| EP | 0 606 566 B1 | 12/2001 |
| WO | WO 99/57539 A1 | 11/1999 |

OTHER PUBLICATIONS

International Search Report dated Dec. 17, 2013 issued in corresponding International patent application No. PCT/EP2012/076426.

*Primary Examiner* — Erika J Villaluna
(74) *Attorney, Agent, or Firm* — Ostrolenk Faber LLP (57) ABSTRACT

A method and a device that determines surface characteristics of a stent to be implanted in a lumen in a body in which a wetting behavior of a stent surface serves as measure for the surface characteristics of the stent surface. In order to determine the wetting behavior, a course of a wetting force along a length of the stent surface is determined, the wetting power between the stent surface and a liquid surface being detected along the length of the stent.

20 Claims, 6 Drawing Sheets

(51) Int. Cl.
*A61F 2/00* (2006.01)
*A61F 2/89* (2013.01)
*A61F 2/95* (2013.01)
*A61F 2/86* (2013.01)

(52) U.S. Cl.
CPC ................ G01N 13/02 (2013.01); *A61F 2/86* (2013.01); *A61F 2002/0086* (2013.01); *A61F 2240/001* (2013.01); *A61F 2240/008* (2013.01)

(56) References Cited

U.S. PATENT DOCUMENTS

| | | | |
|---|---|---|---|
| 6,286,368 B1* | 9/2001 | Solomon | B23K 3/0669 73/437 |
| 2003/0099684 A1* | 5/2003 | Domb | A61L 31/10 424/426 |
| 2004/0187565 A1 | 9/2004 | Sutton | |
| 2008/0086198 A1 | 4/2008 | Owens et al. | |
| 2009/0105809 A1 | 4/2009 | Lee et al. | |
| 2011/0002868 A1* | 1/2011 | Bierganns | A61K 8/737 424/70.13 |
| 2011/0178590 A1 | 7/2011 | Zuckct | |

* cited by examiner

METHOD AND DEVICE FOR DETERMINING SURFACE CHARACTERISTICS OF STENTS, AND STENT HAVING DEFINED SURFACE CHARACTERISTICS

CROSS REFERENCE TO RELATED APPLICATIONS

The present application is a 35 U.S.C. § 371 National Phase conversion of PCT/EP2012/076426, filed Dec. 20, 2012, which claims benefit of Swiss Application No. 00049/12, filed Jan. 11, 2012, the disclosure of which is incorporated herein by reference. The PCT International Application was published in the German language.

TECHNICAL FIELD OF THE INVENTION

The present invention relates to a method and a device for determining surface characteristics of a stent for implantation in a body lumen as well as a stent with defined surface characteristics and an arrangement with such a stent and an insertion device for insertion of the stent into body lumen.

BACKGROUND OF THE INVENTION

Vascular prostheses and implants in the form of stents are known from the state of the art to a large extent. Essentially a distinction is to be made between balloon-expanding or self-expanding stents, which, by means of an insertion device, such as for instance a catheter, are inserted into a body lumen. Common to all stents is that, for insertion into a body lumen, they must have a more minimal diameter than in the exercising of their function in the body. As a rule, the stents are delivered and packaged in a compressed state under so-called cleanroom conditions. A cleanroom is a room in which the concentration of particle is continuously monitored. Cleanrooms are categorized in various classes, so-called ISO classes; thus e.g. in a cleanroom of the class ISO-7, the number particles that are 0.5 micrometer in size may not be more than 352 000 per cubic meter. For 1.0 micrometer the upper limit is 83 200 and for 5.0 micrometer 2930 particles per cubic meter (according to DIN EN ISO 14644). Particles smaller than 0.5 micrometer are not taken into consideration in this class. Such an ISO-7 cleanroom is often used for medical implants, such as e.g. stents.

A cleanroom for producing and preparing stents on catheters is thus not 100% free of particles. Moreover, in particular for stents and catheter many production steps are carried out manually. Since, as a rule, the human being is the greatest source for particles and other contamination, a suitable packaging helps to keep the specified cleanroom class.

The stents implanted in blood vessels entail certain risks for the patient. Among other things, inflammatory reactions and/or development of thrombosis on the structures of the stent lead to a renewed stenosis in the blood vessels. Complications of this kind are caused inter alia by soiling of the stent, i.e. its surface, the implant device or other elements that come into contact with the stent, during insertion of the stent into the body lumen. The stent and the insertion device should therefore be as free as possible of any contamination, i.e., for example, have no dust, no fibers, chemical impurities (such e.g. hydrocarbon compounds, residue from electropolishing processes, etc.) or particles in general.

Such contamination can arise with conventional methods for preparation of a stent for implantation e.g. also after a surface treatment and cleaning of the stent, during crimping or insertion on or in a catheter. For example, "naturally" occurring contamination, caused by work carried out in the cleanroom e.g. by work gloves or diverse particles from the atmosphere, can remain adhered to the stent. By means of optical controls after stent mounting on the catheter any particles can be noticed and, if need be, be removed using a clean gas (e.g. oil-free and particle-free, ionized air) flowing out of a nozzle.

The success of the treatment of a body lumen, such as e.g. a coronary artery, using a stent is consequently significantly dependent on the surface characteristics of the stent. Known from US 2008/0086198 A1 is a stent with a nanoporous surface layer, which should improve the ingrowth of the stent and its re-endothelialization and reduce inflammation and an intimal proliferation. The nanoporous surface layer with one or more therapeutic active substances can thereby be provided in order to improve further the described functions of the stent. There are numerous examples of active substance layers, inter alia hydrophilic or hydrophobic active substance layers are generated on the stent surface. Furthermore, shown in FIGS. 24 to 26 are experimental results for stents with a controllable elution system, which has a more minimal restenosis compared with stents with bare metal surface (bare metal stents). The reduced degree of restenosis with a stent with nanoporous surface is attributed to an improved biocompatibility and an improved complete healing of the body tissue. In contrast thereto, with simple metal surface, a chronic irritation of the tissue surrounding the Stent is presumed. No conclusive studies have been made concerning the purity of the stent surface.

Soehnlein et al. (Neutrophil-Derived Cathelicidin Protects from Neointimal Hyperplasia; Sci Transl Med 3, 2011) shows a stent having a protein coating with the protein cathelicidin (LL37). The ingrowth behavior of the coated stents was tested in trials on animals. The trials showed a more minimal restenosis, and it is suspected that cathelicidin promotes and regulates the Re-endothelialization, and thereby protects against a neointimal hyperplasia following the stent implantation. The use of coatings on stents generally has drawbacks however. For example, the surface friction of the stent can be increased; the coating can be damaged with expansion of the stent (tearing, bursting, etc.) or can bring about negative side effects involving blood circulation.

Known from EP 0606566 B1 is a method for producing implant surfaces in which the surfaces of the implant are plasma-treated. With plasma treatment, contamination layers, such as for instance hydrocarbons and other particles deposited from the environment can be removed. The preparation of the stent thus takes place in a chamber with cleanroom conditions.

Although the stent surface can namely be cleaned with a cleaning process in the said methods, the purity of the stent surface thereby corresponds at best to the cleanliness classes of the cleanrooms applied. A higher cleanliness with lesser contamination than corresponding to this cleanliness class cannot be achieved with these methods.

For characterization of the metal surface of implants, various measuring methods are known, such as for example the measurement of the electrophoretic mobility, the measurement of the surface charge by means of acid base titration, the impedance spectrometry, voltametry or electron microscopy (REM). By means of REM analysis, e.g. the roughness or grain size of a polished metal stent surface can be viewed. The wetting characteristics of the implant surface can be determined by measuring the angle of contact between liquid and dry metallic surfaces by means of optical methods. Contact angle measurements of this kind are carried out, for example, by application of small drops on one or more selected places of a surface to be measured and subsequent optical recording of the wetting behavior of the surface. However only a punctual examination of the wetting features can thereby take place. It is not possible to analyze the entire surface.

These known methods for examination of the surface characteristics are either very complicated and costly, or can capture only a small portion of the surface or are unsuitable for complex geometries, such as with a stent, and thus do not allow any examination and characterization of the entire surface of a stent. Furthermore extremely small particles, such as carbon contaminants from the environment, below a certain degree of contamination, can hardly be registered.

Known from material analysis are analytical methods having a higher precision than the above-mentioned methods. Used for characterization of the surfaces is thereby X-ray photoelectron spectroscopy (XPS), the energy-dispersive X-ray spectroscopy or a mass spectroscopy method (e.g. Time-of-flight Secondary Ion Mass Spectroscopy Method (TOF-SIMS)). These methods are hardly suited for simple determination of the purity of a stent surface, however. In particular they are not advantageous for detection of contaminants, which e.g. consist of hydrocarbon compounds, for distinguishing between stents prior to and subsequent to a cleaning, and, if necessary after further manipulative steps. For carrying out analyses of this kind, the stents must be prepared according to analysis requirements, whereby a contamination of the stent surface can take place within the range of contamination to be measured. Furthermore it is hardly possible to create an analysis room that itself does not contribute to contamination of the stent surface. Moreover methods of this kind are very complicated and costly.

SUMMARY OF THE INVENTION

It is an object of the present invention to provide a method and a device for determining surface characteristics of a stent which enables a reliable evaluation of the surface quality, in particular a reliable indication of the purity of a stent surface, which method and device are also suitable for applications requiring high levels of cleanliness, and which make possible a simple and quick determination of surface characteristics. Furthermore a simple measuring method for quality control should be provided which can be used e.g. cost-effectively and efficiently e.g. after a stent production process.

Furthermore it is an object of the invention to provide a stent with defined surface characteristics and an arrangement of such a stent and an insertion device that reduce the complications in the use of the stent in the body lumen, in particular improve a desired ingrowth of the stent in the body lumen and prevent a restenosis.

These objects are achieved by the invention through a method and a device for determining surface characteristics of a stent as well as a stent and an arrangement according to the claims. Preferred embodiments and various embodiment examples are described in the dependent claims.

Stents have essentially a proximal end and a distal end, a stent lumen with compressible or respectively expandable diameter extending between the ends. Stents have, as a rule, a mesh-like structure which is composed of bar segments. Individual bar segments can thereby be connected into a stent or the bars can be created by cutting out of a solid material. It is also possible to shape a wire e.g. into a zigzag structure. A mesh structure can thereby be formed e.g. from the wire, which is coiled up into a tubular shape. Before the insertion into a body lumen in expanded and/or compressed state the stent usually forms a regular mesh structure with a periodically repetitive mesh structure. An inventive method and such a device are suitable for any kind of stents for determining surface characteristics of the stent. With bare metal stents having smooth surface in particular, they are especially advantageous since said stents are especially susceptible to contamination from ambient atmospheres. However also with coated stents the method can also be advantageously used.

In principle the method according to the invention is limited to stents and can generally be used with elongated implants, such as e.g. also with so-called coils or wound forms, which are implanted for treatment of aneurysms. The method can thereby determine surface characteristics of the implants qualitatively and quantitatively.

With a method for determining surface characteristics of a stent for implantation in a body lumen according to the present invention, a wetting behavior of stent surface serves as the measure for surface characteristics of the stent surface. The wetting behavior is determined along a length of the stent surface through determination of a course of a wetting force, whereby the wetting force situated between the stent surface and a liquid surface is detected along the stent length. The wetting force can thereby be measured according to the principle of tensiometry, in that the force behavior is measured at various places spaced apart in longitudinal direction of the stent. Preferably a dynamic measurement is carried out along the stent length. Based on the thereby determined wetting behavior course along the stent length, the stent surface can be characterized overall.

The wetting behavior of the stent surface can be determined using a device for determination of surface characteristics of a stent according to the present invention. The device constitutes a measurement device of tensiometric type. The determining device has a liquid container with a defined liquid, i.e. with a specified surface tension, liquid container and liquid having together a reference weight. Furthermore the determining device has a measurement device for measuring a deviation from the reference weight as the measure for a wetting force of the stent surface and a movable holding device for holding the stent and moving the stent substantially in direction of the longitudinal axis of the stent. The holding device is intended to at least partially submerge the stent in the liquid of the liquid container. Preferably is immersed almost completely under the liquid surface and in the liquid. Furthermore the determining device has a processing unit for determining the deviation measurement of the measurement device and determining a course of a wetting force along a length of the stent surface. Thus a change in the wetting force can be determined acting on the stent surface in the region of the liquid surface, while the stent is submerged by the holding device and pulled out of said through the liquid surface. The course of the change in the wetting force can thereby be determined along the stent length.

In the sense of the invention the liquid container can also in principle be moved with measurement device relative to a stationary stent, or only the liquid container relative to the stent and to the measuring device.

The method and the device according to the invention enable a qualitatively as well as quantitatively evaluation of an overall stent surface and the local assignment of measuring results along the length of the stent. More information about an overall surface can be determined, compared with statistical measurements of the wetting behavior, since with statistical methods only small or even punctual areas are examined. By means of the inventive method, on the other hand, determination of the entire structure of a stent is possible without great effort. This is especially also possible in particular with only very minimal contamination, which can be detected only with great effort (if at all) using known methods and leads to a reliable indication e.g. about the cleanliness or respectively the degree of contamination of the stent surface. The inventive method constitutes a simple method of measuring for quality control, e.g. following a stent production process, which can be used cost-effectively and efficiently. Such a control is not possible using methods based on a measurement of contact angle.

The determination of the course of the wetting force takes place preferably dynamically along a significant length of the stent, preferably over a length comprising at least a plurality of periods of the mesh structure. Good measurement results are obtained with a measurement over substantially the entire stent length. The dynamic measurement takes place in that the stent is moved preferably into the liquid through the liquid surface at predetermined speed. It is thereby advantageous to dry the stent prior to the immersion, i.e. before the measurement, if this stent was located in a fluid or humid environment i.e. before the measurement or e.g. has been rinsed with pure water. During immersion a curved liquid meniscus forms owing to the surface energy of the stent surface, which meniscus abuts the stent surface. The liquid meniscus is shaped depending upon the surface tension of the liquid and of the surface properties and condition (surface energy, roughness, etc.) of the stent; depending upon degree of surface tension of the stent surface, compared with the surface tension of the liquid, the liquid is attracted to or repelled by the stent. In the case of a hydrophilic surface with high surface energy, a liquid, such as water, is attracted. And in the case of a hydrophobic surface with low surface energy, the liquid is repelled, as soon as e.g. the free end of the stent contacts the surface of the liquid or is immersed in the liquid. The reference weight thereby changes correspondingly on the measurement device. A characteristic wetting force along the length of the stent surface is generated by means of the surface energy with the movement of the stent through the liquid surface. The wetting force thus depends on the contact area between stent surface and liquid surface, the selected liquid as well as the surface properties and condition and the material of the stent surface.

The wetting force course along the length of the stent surface is furthermore dependent upon a structure, such as a certain mesh structure, and has a periodicity corresponding to the stent structure (the so-called strut segments). The contact area thus changes corresponding to the mesh structure of the stent during immersion in or removal of the liquid and repeats itself periodically according to the periodicity of the mesh pattern of the stent. Furthermore the surface energy and thus the wetting force changes with surface properties and condition; in particular the surface energy changes with degree of contamination of the stent surface. Also the roughness and the porosity influence the arising wetting force. The wettability and the wetting force correlate with the concentration of contamination particles and molecules. The surface of a metal stent, having in principle a hydrophilic surface, becomes more hydrophobic the greater the degree of contamination.

The change of the liquid meniscus through change of wetting force engaging the stent surface has as a consequence a change in the weight acting upon the measuring device from the liquid container and the liquid. The deviation from the reference weight, i.e. from the weight of container and liquid without influence of a wetting force is thus characteristic for the course of a wetting force along a length of the stent surface. The course of the wetting force can therefore be measured by the course of weight change relative to the reference weight of the liquid container and of the liquid. The processing unit thus determines the wetting force according to the dynamic measurement of the deviation from the reference weight.

With the deviation measurement, the effect of the wetting force is then shown on the measurement device since the stent held by the holding device is immersed in the liquid from above without coming into contact with the container or measurement device. The weight of the stent thus plays no role based on the Archimedean principle.

The liquid, the mesh structure, the surface topography and the surface material of the stent are constant known factors. Thus, from a change in the wetting force in the case of simple bare metal stent, e.g. conclusions may be drawn about the soiling (contamination) located on the surface. Used thereby for characterizing the stent surface can be e.g. the periodicity or amplitude of a period of the course of the wetting force.

The inventive method and determining device are expedient for determining the purity of a stent surface, in particular for quality control, following a cleaning or during preparation for implantation, and can be carried out without great effort and preparation of the stent. Furthermore the consistency of the surface properties and condition of the stent along the stent length can be examined. Irregularities in the course of the wetting force along the stents allow conclusion of a non-uniform condition and indicate (in particular in the case of a smooth, polished surface) an irregularity owing to contamination of the surface. In the case of coated stent e.g. the quality of the coating can be examined.

Used as liquid is e.g. distilled or deionized water. Good measurement results have been obtained with, among other things, water for injection purposes (WFI, Water For Injection). Also distilled water, such as e.g. millipore water is suitable for carrying out the measurement. Advantageously polar liquids with high surface tension are used for measurement, such as water. In principle however a liquid with low surface tension, such as e.g. hexane can be used.

Preferably the course of the wetting force over the entire length and the total circumference of the stent surface is determined. Basically it is also conceivable that a defined area of a stent is dipped in the liquid, such as a stent half. The measuring results for a stent half can be extrapolated for the other stent half.

Preferably used for determining the surface characteristics of the stent, the wetting behavior in relation to a reference wetting behavior of a stent surface. A deviation of the measured wetting behavior from the reference wetting behavior can serve as measurement of surface characteristics of the stent surface. The reference wetting behavior can exist for instance as a theoretical model behavior that is calculated from the known factors for an ideal wetting course of a given stent structure. The reference wetting behavior can however also be determined by averaging from a series of measurements with a multiplicity of comparable stents. Reference courses can thereby be determined which correspond to different degrees of purity of a stent or are assigned to different cleaning steps. Furthermore a stent immediately after a cleaning can be used as reference. This can be used in particular as reference for a stent with such a cleaning and further subsequent manipulation steps, such e.g. compression and packaging. Used as reference furthermore can also be stents with defined hydrophilic or hydrophobic coatings, such as, for example, polymers, medicaments, biomolecules, cells, etc.

In summary, tensiometric-type wetting force measurement is carried out in that the stent is dipped into the liquid container through the liquid surface of the liquid preferably by at least close to its entire surface, and during the dipping into and pulling out through the liquid surface, the course of the wetting force is measured on the stent surface along the length of the stent. It is thereby advantageous if the stent is moved in the liquid along its longitudinal axis in the liquid. In this direction an irregularity in the wetting course can be most easily be attributed to a particular length increment of the stent length. Furthermore it is advantageous when the stent is moved in direction of the greatest frequency of the stent structure. The holding device has for this purpose e.g. a linear drive that moves the stent along its longitudinal axis through the liquid surface.

The stent can thereby be moved at a predetermined speed through the liquid surface and be detected and recorded at regular intervals. The speed can be constant or can correspond to a defined speed profile with different speeds. The speed profile can be harmonized with the stent structure and e.g. have the same frequency. In principle the measurement can also take place during a standstill of the stents at different length increments of the stent length.

With a preferred variant of the method, the wetting force course is determined during immersion of the stent in the liquid. During the immersion an interaction occurs between the liquid surface and the successive respectively newly immersed length increment of the stent surface that has so far not come into contact with the liquid. If the stent is first dipped in and the measurement takes place during the removal, measurement inaccuracies can occur e.g. owing to capillary forces between stent and liquids. This depends on size and diameter of the stent. By means of the capillary forces, the liquid can remain inside the stent and can be pulled upward. Moreover any cleaning effects brought about during the previous immersion of the stent can falsify the measurement results during the removal.

According to the invention, the method and the device is used for determination of the uniformity of surface characteristics of a stent surface along the length of the stent and/or of the purity of the surface, in particular the consistent cleanliness over the entire surface. Thereby used is the dependence of the wetting characteristics of a surface on the cleanliness of a stent. This can be advantageously used in order to examine the cleanliness of a stent after various cleaning procedures and manipulative steps during preparation of a stent for implantation. During the preparation for implantation, the stent can be exposed to diverse natural contamination particles originating from the atmosphere, in particular hydrocarbon compounds. A deposit of such molecules or other particles originating from the atmosphere during the preparation steps can be quantitatively measured and localized with the inventive method. With the proposed method, a change in hydrophilicity or hydrophobicity of the stent surface along the length of the stent can also be determined. The uniformity of the surface is determined among other things by the degree of cleanliness along the entire length of the stent surface and is thus dependent thereon.

Experiments have shown that with the inventive method contamination of the stent surface can be detected which lies far below a particle contamination of cleanrooms normally used for preparation of stents. As initially described, the use of cleanrooms of the class 7 is usual in the preparation and packaging of stents. With the method according to the invention stents having a cleanliness corresponding to thus class and still far cleaner stents can be characterized and quantitatively measured. Such a stent surface can be achieved through manipulation of the stent according to the parallel patent application with the title "Anordnung and Verfahren zur Bereitstellung eines Stents zur Implantation mit Umhüllung" (application number CH 00048/12) and the same filing date of the present application. This application is therefore fully incorporated by reference for disclosure of the invention. Since it shows in what way stent surface characteristics are able to be maintained or achieved until implantation. With the preparation of a stent within a flow of a defined medium in a sheath, a surface cleanliness can be maintained or achieved that is higher than in conventionally used cleanrooms.

Another aspect of the present invention relates to a stent for implantation in a body lumen, comprising a multiplicity of bars which form together a radially expandable tubular form. According to the invention the stent is characterized by an overall surface comprising an outer and inner surface and surfaces between the bars having a uniform or respectively frequency regular surface wetting behavior dependent upon the periodicity/frequency of the stent structure.

Stents with a surface according to the invention have a high degree of cleanliness which is not able to be achieved with conventional stents. Stents as known in the state of the art have even after their preparation for an implantation in a body lumen no uniform or respectively regular surface wetting behavior. They generally have a lesser cleanliness.

Compared with conventionally used stents a uniform stent surface according to the invention improves the behavior of the stent during ingrowth after its implantation and acts against a restenosis. Experimental evidence thereof could also be obtained through an in vivo study in which stents according to the invention are inserted in coronary arteries of pigs and the ingrowth was observed, as will be explained more precisely in the following. As surprising result it could be shown that the ingrowth behavior of stents is considerably more dependent on the cleanliness of a stent than previously assumed. As the measurement results show, the surprisingly good results were obtained with stent treatments with bare metal stents. It was previously assumed that results of this kind could only be achieved with special preparation of the surface, e.g. through coating such as e.g. a medicinal coating. The experiments show however that the success of a treatment of a body lumen using a stent is determined primarily by the cleanliness of the stent.

Preferably the overall surface of the stent has a hydrophilic characteristic and molecular contamination originating from the atmosphere on the overall surface are reduced in such a way by purification that a course of the wetting force along the length of the stent surface has, as measure of the cleanliness of the overall surface, a uniform or respectively regular course. The course of the wetting force can be verified easily and quickly with the method and device of the present invention.

Stents which were packaged and were prepared for implantation after their cleaning with conventional methods could not achieve so far any surfaces with such uniformity and cleanliness that they have a uniform or respectively periodically regular surface wetting behavior over an entire length, as has been able to be experimentally proven. The surface wetting behavior of a stent according to the invention is determined by means of a measurement of tensiometric type, by a verifiable change in weight per length unit of the stent length.

In a preferred embodiment, the overall surface of the stent has a uniform cleanliness having fewer particles per surface unit than corresponds to a conventionally used clean room class (e.g. 7) of the ISO (International Standard Organisation). This means that, with the proposed method according to the aforementioned parallel application, a higher purity of the stent surface can be maintained or achieved than is possible in clean rooms of the highest usually used cleanliness classed without such a cleanroom or also a cleanroom of a lower level being necessary. In particular the stent can also have fewer hydrocarbon molecules and particles of a size below 0.05 micrometer than corresponds to a cleanroom class 1 of the ISO (International Standard Organisation).

According to still another aspect of the invention, an arrangement is proposed of a stent for implantation in a body lumen, as previously described, and an insertion device for insertion of the stent in the body lumen, the stent being stored in or on the insertion device. According to the invention, the surface of the insertion device provided for insertion in the body lumen has a uniform cleanliness corresponding to the cleanliness of the stent. Preferably the insertion device and the stent are stored in an inert environment during further manipulative steps and until an implantation, e.g. in a packaging correspondingly suitable therefor after an implantation cleaning of the stent. It can be therefore assumed that the stent and the insertion device are subjected to the same treatment and thus also to the same surface cleaning.

BRIEF DESCRIPTION OF THE DRAWINGS

An embodiment of the invention is shown in the following with reference to the drawings which serve merely as explanation and are not to be interpreted in a limiting way. Furthermore results from experiments using the method according to the invention are explained. Shown in the drawings are.

DESCRIPTION OF PREFERRED EMBODIMENTS

Figure 1:
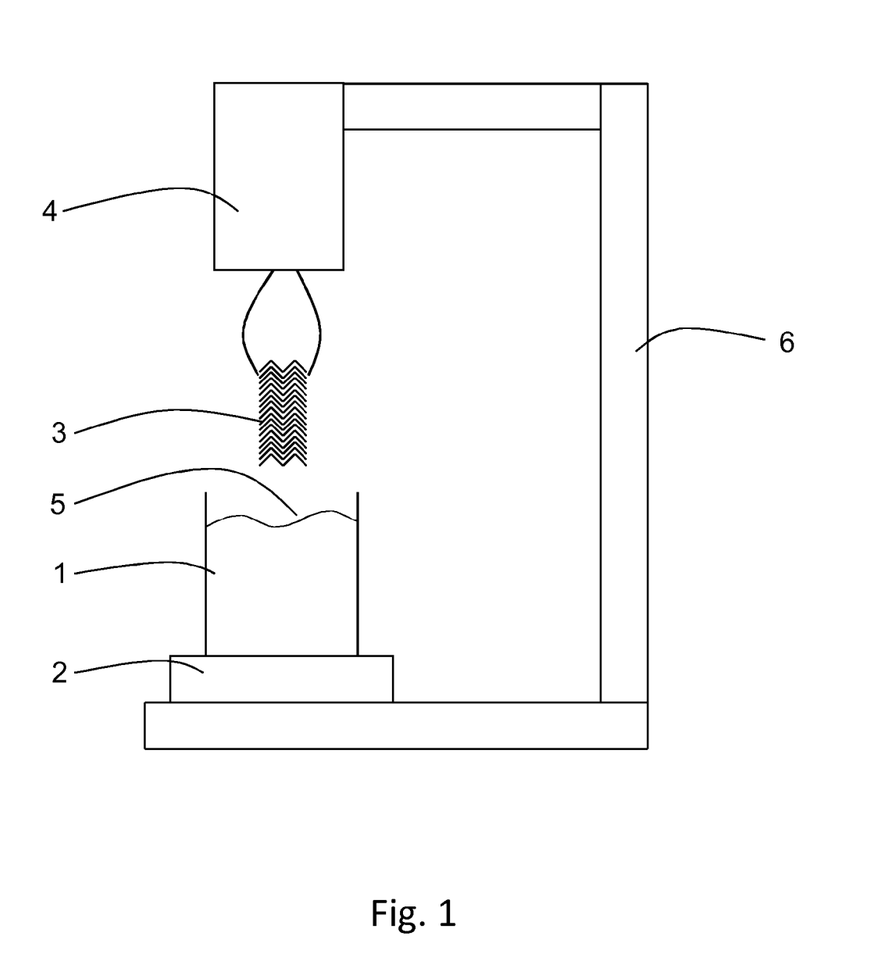
FIG. 1: schematic representation of a determining device according to the invention.

Shown in FIG. 1 is an embodiment of a device for determination of surface characteristics of a stent for implantation in a body lumen according to the present invention. The device is provided to determine a wetting behavior of a stent surface around the circumference of a stent and its length, preferably over its entire length and the course wetting behavior. The device has for this purpose a liquid container 1 with a liquid with a defined surface tension. The liquid container 1 and the liquid have together a reference weight that is measured by a measuring device 2. The size of the liquid container and the liquid volume are coordinated with the measurements of a stent 3. In the embodiment of a meniscus in the case of a hydrophile surface, during immersion or removal of the stents, liquid is elevated or respectively in the case of a hydrophobic surface liquid is repelled. This leads to a significant change of the weight measured by the measuring device. Thereby care is to be taken that the entire liquid quantity in the container is adjusted to a repelled or respectively elevated quantity in order to achieve a significant change of the weights. The measuring device determines such a deviation from the reference weight as measurement for a wetting force of the stent surface. Suitable as measuring device is e.g. an analytical laboratory scale with measurement range between minus 200 and plus 200 gram and a precision of von 0.3 milligram.

Furthermore the determining device has a movable holding device 4 holding of the stents and movement of the stent in a direction substantially along the longitudinal axis of the stent, which is intended to dip the stent 3 into the liquid at partially. The holding device can have e.g. a clamp which is gripped with the stent at one end. The rest of the stent 3 hangs down freely from the holding device 4 in direction of the liquid surface 5. For dipping of the stent e.g. a linear motor is provided that is able to move the stent preferably in direction of its longitudinal in vertical direction. This linear motor can be integrated in the holding device 4. The holding device is for example provided on a support frame 6 which is disposed around the liquid container and has at least one arm which projects over the liquid surface and is provided with the clamp.

Moreover the determining device has a processing unit (not shown) for registering the deviation measurement of the measuring device 2 and determining a course of a wetting along a length of the stent surface. The processing unit can be e.g. by means of a computer which records and processes the measurement data of the measuring device. The processing unit also serves for control of the holding device, or respectively of the linear motor and control the speed of the stent movement during a measurement. Furthermore a comparison of the measurement curve can be carried out by the processing unit and a deviation from the reference determined.

In the case of moist or wet stent or in the case where the stent has to be rinsed, it is completely dried prior to carrying out a measurement of the wetting force course, e.g. blown dry with nitrogen of the quality 5.0. The determination of the course of the wetting force can be carried out basically during dipping of the stent or during removal of the stents through the liquid surface. A measurement during the dipping of the dry stent has however the above-mentioned advantages. The stent 3 is moved at a defined, preferably constant, speed (e.g. 70 micrometer per second) through the liquid surface 5. At preferably regular intervals, of e.g. a second, the total weight of liquid container 1 and liquid is measured with effect of the wetting force determined and the deviation from reference weight recorded. Thus a measurement value is determined per length increment of the stent length, which indicates the wetting force of the stent surface. Thus a measurement value can be precisely assigned to a length increment.

Figure 2A:
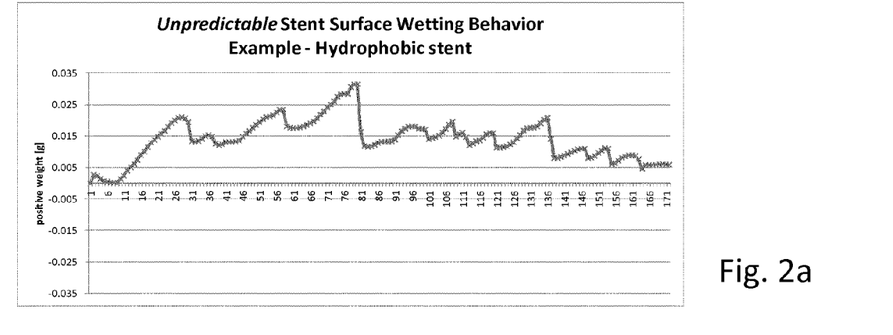
FIG. 2a: measurement result of a determination of the surface quality of a highly contaminated stent.
Figure 2B:
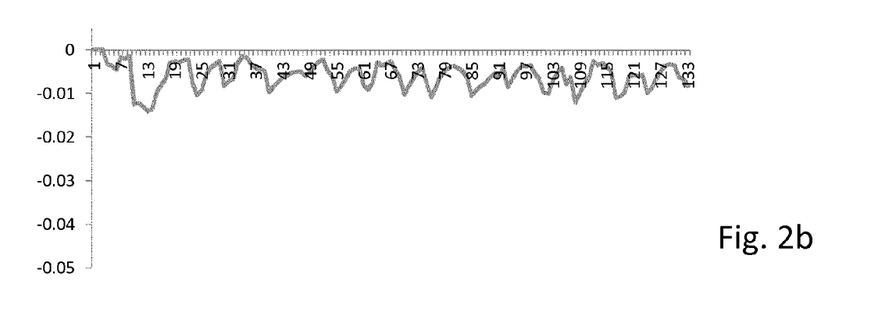
FIG. 2b: measurement result of a determination of the surface quality of a stent following a conventional production, cleaning and storage.
Figure 2C:
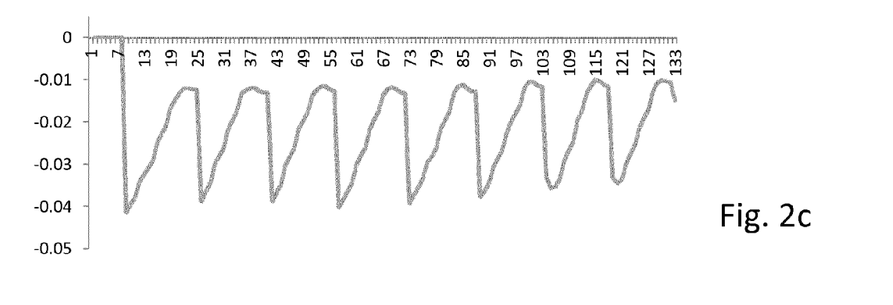
FIG. 2c: measurement result of a determination of the surface quality of a stent, as in FIG. 2b, after another cleaning treatment or respectively a preparation according to the invention.

The FIGS. 2a, 2b and 2c shows respectively a measurement of the course of the wetting force on conventionally prepared stents (FIGS. 2a and 2b) and on a stent with uniform surface properties and condition (FIG. 2c). The stent in FIG. 2c underwent an additional cleaning procedure in the form of a plasma cleaning method. Further measurements have shown that according to a preparation method according to the invention the same surface quality is obtained. The measurements (FIGS. 2a, 2b and 2c) are based on the same commercially available bare metal stents of the manufacturer Fortimedix of the size 3×19 mm. Used as liquid was pure water (WFI); thus Information about the hydrophilicity of the stent surface could also be obtained. Shown in the figures the x axis indicates the time axis during the dipping or respectively the length of the stent and the y axis a weight deviation, or respectively change in wetting force. The curves thus show the course of the wetting force along a length of the stent surface. The course of the wetting force was determined during dipping of the stent into the liquid surface.

The stent in FIG. 2a has a periodic structure and was kept in a test tube until measurement, whereby it was exposed to diverse contaminants after production, such as e.g. dust, silicon contaminants, floating particles, etc. The stent was measured without prior cleaning. As seen in FIG. 2a, the stent displays a stochastic course of the wetting force without regular change. It can be seen therefrom that the stent has no uniform surface quality. Furthermore the measurement for the overall length of the stent is to a large extent above a neutral value for a measurement at zero, the neutral value corresponding to a measurement without penetration of the stents into the liquid surface. This indicates a hydrophobic quality of the surface and thus a high level of contamination of the surface.

The stent with measurement results from FIG. 2b was produced in a cleanroom, cleaned after the production, and kept in a cleanroom-suitable glass tube as packaging, as is usual in the state of the art. For measurement, the stent was taken out the packaging and analyzed with the method for determining its surface characteristics according to the present invention. The course of the wetting force lies only just under the neutral value. Other measurements of other stents of the same Type and same production and packaging methods have shown that the course of the wetting force lies in the positive range (i.e. between the values of FIGS. 2b and 2a). From this it can be concluded that a contact angle of the wetting between lies at 70 and 90 degrees or more and the stent therefore has more of a hydrophobic behavior. The curve course shows a roughly repetitive behavior, but however with different marked maxima and minima, different amplitudes and with different slopes. It will be seen from the minimal deviation from the neutral value and the irregular wetting course that the stent has no uniform, periodically regular surface wetting behavior. Furthermore this points to an medium degree of contamination. Furthermore this points to natural contamination of hydrocarbon compounds out of the atmosphere.

The stent in FIG. 2c underwent a plasma cleaning and was stored inside an inert medium, so that the stent has a uniform and pure surface quality. The course of the wetting force along the stent length shows a clear periodicity corresponding to the periodicity of the mesh structure of the stent. Within a periodicity the effective wetting force changes corresponding to the surface of the stent segments that interact with the liquid surface on a particular length increment. Depending on the attack surface of the liquid on the stent, the greater the change is in the wetting force. Based on the regular repetition of a mesh period, a regular rise and fall of the wetting force thereby takes place. The amplitude and the length of the periods are substantially the same. Furthermore slope and fall of the individual amplitudes coincide. It follows therefrom that the stent has a uniform quality of the surface. Furthermore the curve lies clearly below the neutral niveau, which points to a hydrophilicity of the stent surface. From the measurement a hydrophilicity can be concluded having a contact angle below 15 degrees. The stent surface can thus be considered as highly hydrophilic.

For stents according to FIGS. 2b and 2c contact angle measurements were carried out as comparative measurements for contact angle determination. The comparative measurements were carried out on smooth surfaces comparable with the surface of the stents. Contact angle measurements were carried out on the following probes: disks with 15 mm diameter, electropolished surfaces, i.e. equivalent to stent surface in quality and material.

Same results as in FIG. 2c were obtained also for a stent which was handled according a preparation method according to the invention.

Figure 3A:
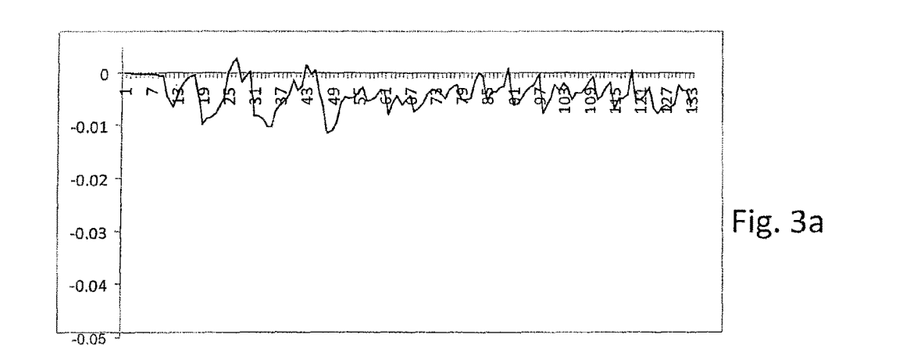
FIG. 3a: measurement result of a determination of the surface quality of another stent following conventional production, cleaning and storage.
Figure 3B:
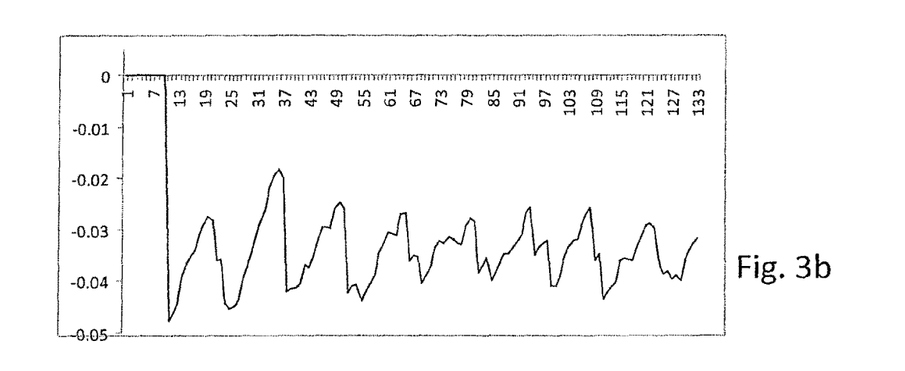
FIG. 3b: measurement result of a determination of the surface quality of the stent, as in FIG. 3a, following another cleaning treatment.

FIGS. 3a and 3b show a measurement of a stent with a mesh structure which winds spirally about the axis of the stent. The periodicity along the stent axis is therefore less marked than with a stent used for the measurements according to FIGS. 2a, 2b and 2c having mesh structure running symmetrically to the longitudinal axis. The measurements according to FIGS. 3a and 3b are each based on a same commercially available stent of the producer Medtronic of the size 3×18 mm. The stents were mounted on a balloon catheter, packaged and sterilized by the producer in a cleanroom. As mentioned above, the change in weight measurement depends on the type of surface. With hydrophobic surfaces the weight measured by means of water increases and with hydrophilic surfaces the weight measured by means of water decreases during dipping. Thus the weight change makes possible a statement about the hydrophilicity or hydrophobicity of the stent surface. With bare metal stents the hydrophilicity correlates with its purity.

In FIG. 3a a stent was analyzed that was just removed from its sterile packaging and from the balloon without a further cleaning having taken place. It was expanded to 3 mm and analyzed according the method of the present invention for determining its surface characteristics. As is to be learned from the curve, the fluctuations of the wetting force along the stent surface are comparatively minimal and lie just below the neutral niveau. Used in FIG. 3b was the same stent, subjected however additionally to a plasma treatment for cleaning of the stent. The curve shows a clearly elevated hydrophilicity compared with the stent from FIG. 3a, and, to be precise, over the entire stent length, since a clear shift into the negative region has taken place. Furthermore the surface quality is consistently formed since a regular repetition is shown, corresponding to the mesh structure, of the wetting force change over the entire stent length. Same results as FIG. 3b were obtained also for a stent handled according to the inventive preparation method.

Figure 4A:
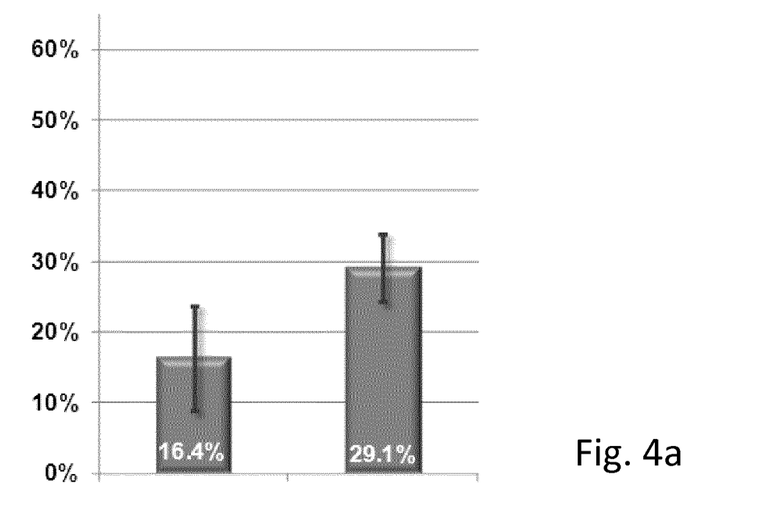
FIG. 4a: graphic representation of an in-vivo X-ray analysis (angiography) of a first stent according to the invention.
Figure 4B:
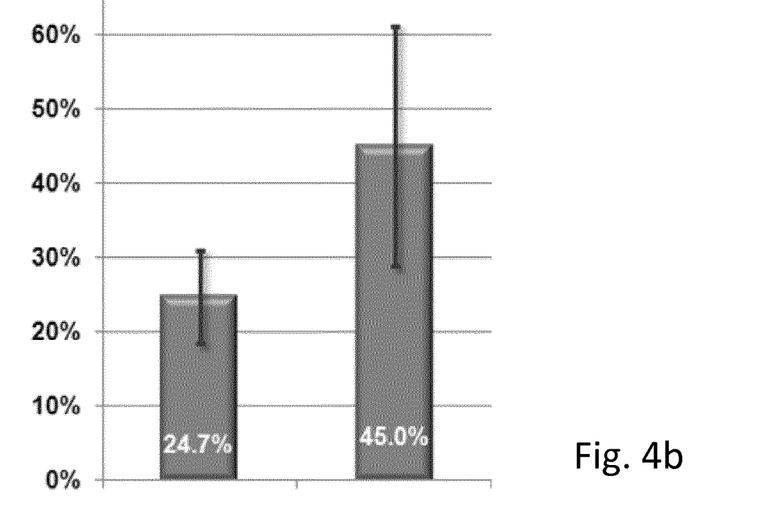
FIG. 4b: graphic representation of an in-vivo X-ray analysis (angiography) of a second stent according to the invention, FIGS. 5a, b, c: Depiction of a histomorphometric analysis of a stent with uniform cleaning according to the invention, FIGS. 6a, b, c: Depiction of a histomorphometric analysis of the same stent type as in FIGS. 5a, b, c with conventional cleanliness

Shown in FIGS. 4a and 4b are the results of animal studies obtained with insertion of stents in coronary arteries in pigs. The most minimal vascular diameter in the region of the stent was determined after the insertion of a stent into an artery and determined thirty days after the insertion and ingrowth. After insertion of the stents the diameter of the stent reduces owing to the ingrowth of cells in the region of the stents. The vascular diameter is thereby measured angiographically, i.e. by means of X-ray analysis. The study comprises a measurement series of eight comparative trials.

Used in FIG. 4a was the stent of Medtronic (3×18 mm) with a spiral mesh structure which was ready for implantation in a body lumen. The left beam shows the behavior of such a stent in the body lumen after a preparation according to the invention with a uniform surface wetting behavior, and the right beam such a stent immediately from the packaging without further treatment steps, as it is conventionally used. It is clearly seen that the stent according to the invention with a uniform surface shows an improved ingrowth behavior, in contrast to a conventionally prepared stent. An undesired resteninosis can be reduced in this example with a stent according to the invention from 29.1% to 16.4%, i.e. by about 44%, this being statistically significant ($p=0.009$).

Used in FIG. 4b was a stent of Abbott of the size 3×18 mm which had a regular symmetrical, i.e. not helical, mesh structure and was ready for implantation in a body lumen. The left beam shows again the behavior of such a stent in the body lumen after a preparation according to the invention and the right beam such a stent immediately out of the packaging without further treatment steps, as conventionally used. Also the stent with this mesh structure shows following a preparation according to the invention a clearly improved behavior during ingrowth in the artery with a clearly reduced narrowing of the diameter by 45% to 24.7%, i.e. by about 45%, this being statistically significant ($p=0.024$).

From these results it clearly follows that the use of a stent according to the invention with a uniform, or respectively periodically regular surface wetting behavior compared to commonly available stents shows a clearly improved ingrowth behavior and less restinosis. According to the invention are therefore bare metal stents with a uniform, or respectively periodically regular surface wetting behavior, i.e. highly pure stents for the implantation in body lumina.

Figure 5A:
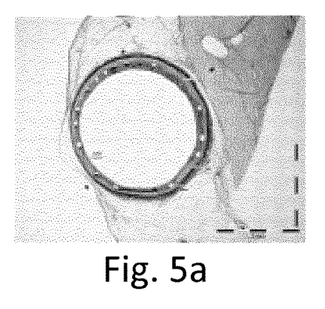
Figure 5B:
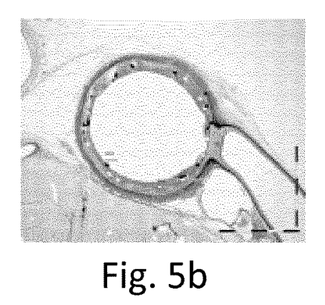
Figure 5C:
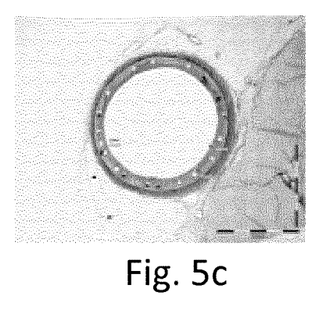

Shown in FIGS. 5a, 5b and 5c as well as 6a, 6b and 6c is the cross section of a coronary blood vessel of a pig, after it was examined 30 days after the insertion of a stent of Medtronic, as is usual for histological examinations. The original vessel edge is identified and then the cross-sectional area of the ingrown cells calculated, from which a percentual growth rate, results, i.e. the endothelialization or respectively stenosis rate.

Used in FIGS. 5a, 5b and 5c is a stent according to the present invention with a uniform and highly pure surface, as can be verified according to a measurement as shown e.g. in FIG. 3b. FIG. 5a shows the ingrown stent in a proximal region of the blood flow, FIG. 5b in a central region with a bifurcation and FIG. 5c in a distal region of the blood flow. As can be seen, there is only a minimal reduction of the diameter of the artery owing to growth. Moreover there is an even ingrowth of the stent.

Figure 6A:
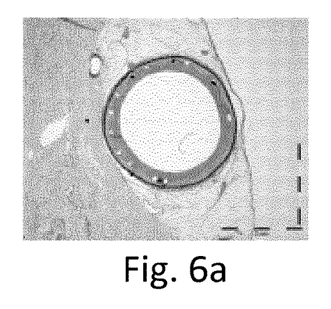
Figure 6B:
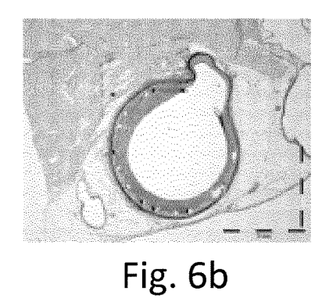
Figure 6C:
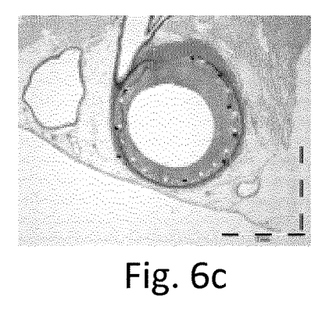

Used in FIGS. 6a, 6b and 6c is a conventional stent, as based e.g. on a measurement according to FIG. 3a. Both in the proximal region (FIG. 6a), in the middle area (FIG. 6b) as well as also in the distal region (FIG. 6c) the diameter was more constricted than with the stent out of the FIGS. 5a, 5b and 5c. In particular in the distal region a strong restinosis can be demonstrated.

As can be learned from the figures, through a uniform and pure stent surface the risks can be considerably reduced with the treatment of vascular diseases. Moreover it is possible with the method and the device according to the invention, to determine the surface characteristics of stents according to a production method or after a particular preparation process reliably and without great effort or cost. Thus stents showing no sufficiently good surface characteristics can be excluded from an implantation.

There follows in FIGS. 7a to 7e a schematic depiction of the individual steps during the ingrowth of a stent, as has been able to be identified with trials of the applicant. Shown are individual steps with a conventional bare metal stent 3' (above) and a highly pure bare metal stent 3 according to the present invention, in particular with a stent with a uniform, or respectively periodically regular, surface wetting behavior over the entire length. As described, such a highly pure stent can be achieved e.g. through a method and an arrangement according to the patent application of the applicant with the title "Anordnung and Verfahren zur Bereitstellung eines Stents zur Implantation mit Umhöllung" (application number CH 00048/12). Viewed in the example according to the FIGS. 7a to 7e is a stent with a highly hydrophile surface.

Figure 7A:
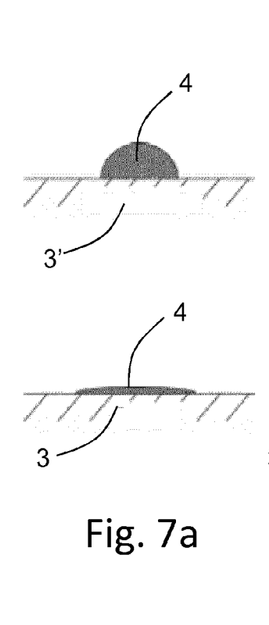
FIGS. 7a to 7e: schematic course of the ingrowth of a conventional bare metal stent (above) and a highly pure bare metal stent according to the invention (below).
Figure 7B:
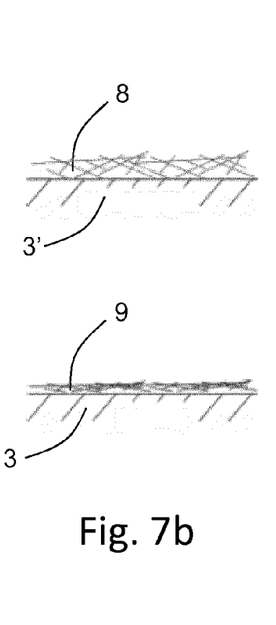
Figure 7C:
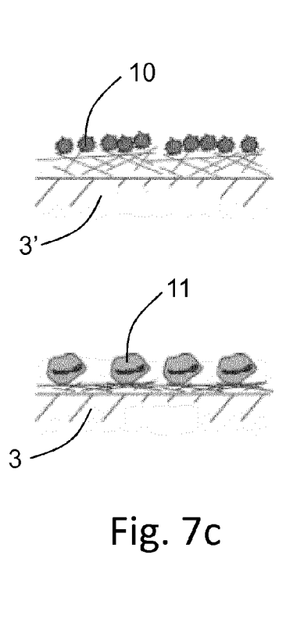
Figure 7D:
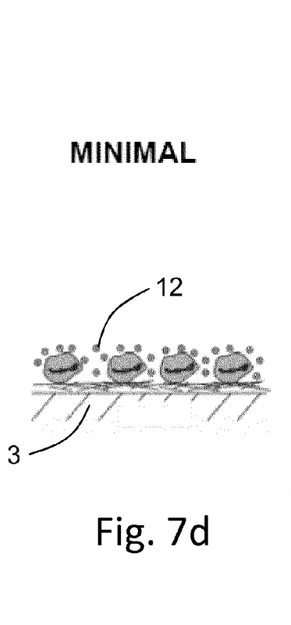
Figure 7E:
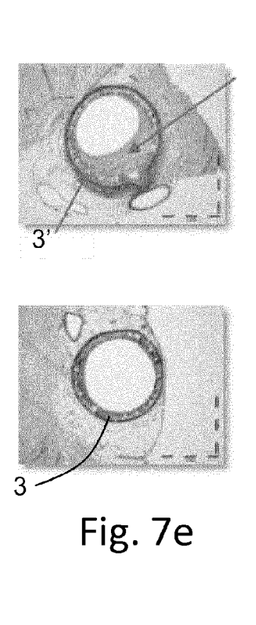

Shown in FIG. 7a is the wetting behavior of a water drop 7 on the stent surface. On the conventional stent 3' (FIG. 7a, above) there is a large contact angel while with the highly pure stent 3 (FIG. 7a, below), owing to the hydrophile surface characteristics, only a very minimal contact angle. In FIG. 7b the stent is placed at the place of implantation and the viewed surface is exposed with respect to the blood. With the conventional stent 3' (FIG. 7b, above) there takes place at first a deposit of proteins, that both adhere as well as also impede the functionality of neutrophiles (FGN, A2M, ApoA), so-called neutrophile inhibitors 8. With the highly pure stent 3 (FIG. 7b, below) the neutrophile inhibitors 8 (FGN, A2m and ApoA) are greatly reduced and at the same time proteins are deposited that prevent the adhesion of thrombocyte s(HMWK) as well as proteins that promote the adhesion of neutrophiles on the stent surface (PGN) so-called neutrophile promoters 9. Correspondingly, in the case of the conventional stent 3' (FIG. 7c, above), thrombocytes 10 mainly settle on the neutrophile inhibitor 8, which are in principle undesired. With the highly pure stent 3 (FIG. 7c, below), on the other hand, neutrophile cells out the blood of the patient settle on the neutrophile promoters 9, while thrombocytes are repelled. The activated neutrophile cells 11 separate the protein cathelicidin (LL37) 12 on the stent surface, cf. FIG. 7d below. The process of the ingrowth can thereby be positively supported without a coating or a medicament delivery being necessary for this purpose. With the conventional stent 3' cathelicidin was found in only very minimal quantity. The trials have shown that the highly pure stent 3 two to three times more cathelicidin accumulates than with the conventional stent. The highly pure stent 3 with a regular surface wetting behavior shows an ingrowth behavior that is comparable with that of FIGS. 5a to 5c (see FIG. 7e, below). The conventional stent 3' shows however an ingrowth according to FIGS. 6a to 6c, i.e. again a narrowing of the passage (see FIG. 7e, above). In summary, it can be stated: the highly pure surface of the stent 3 supports and promotes those bioactive processes that lead to

LIST OF REFERENCE NUMERALS 1 liquid container
2 measuring device
3, 3' stent
4 holding device
5 liquid surface
6 holding frame
7 water drop
8 neutrophile inhibitors
9 neutrophile promoters
10 thrombocytes
11 neutrophile cells
12 cathelicidin

What is claimed is:

1. Method of determining surface characteristics of a stent for implantation in a body lumen, in which a wetting behavior of a stent surface serves as measure for the surface characteristics, comprising: detecting a wetting force between the stent surface and a liquid surface along a length of the stent; determining a course of a wetting force along the stent surface; determining the wetting behavior of the stent surface; and determining the surface characteristics of the stent based on the wetting behavior of the stent surface.

2. Method according to claim 1, wherein the stent surface for detecting the wetting force by liquid surface is moved.

3. Method according to claim 1, wherein a change in the wetting force is detected, while the stent surface is moved by the liquid surface.

4. Method according to claim 1, wherein the course of the wetting force is detected substantially over the entire length and the entire circumference of the stent surface.

5. Method according to claim 1, wherein the course of the wetting force along the length of stent surface depends on a stent structure and has a periodicity corresponding to the stent structure, the periodicity or amplitude of at least one period of the course being used for characterizing the stent surface.

6. Method according claim 1, wherein the wetting behavior is set in relation to a reference wetting behavior of the stent surface and a deviation from the reference wetting behavior serving as measure for the surface characteristics.

7. Method according to claim 6, wherein the reference wetting behavior is made up by a wetting behavior of a stent measured immediately after cleaning treatment.

8. Method according to claim 1, wherein the wetting force is detected dynamically by a method of tensiometric type.

9. Method according to claim 1, wherein the method of tensiometric type is carried out comprising the steps of:
a stent surface is submerged in a liquid container through a liquid surface of a liquid and
during submerging or removal of the stent through the liquid surface the course of the wetting force is detected on the stent surface along the length of the stent.

10. Method according to claim 9, wherein the course of the wetting force by means of a course of a change in weight of the liquid container and the liquid are detected.

11. Method according to claim 9, wherein the stent is moved at constant speed in direction of the longitudinal axis of the stent through the liquid surface and at regular intervals a change in weight is detected and recorded.

12. Method according to claim 1, wherein the stent is dried and during the course of the wetting force along the stent surface, the entering of the stent into the liquid surface is detected.

13. A method for determining the uniformity of surface characteristics of the stent surface along the length of the stent and/or the purity of the stent surface and/or a change in a hydrophility or hydrophobicity of the stent surface along the length of the stent with a method according to claim 1.

14. Device for determining surface characteristics of a stent for implantation in a body lumen, which detects a wetting behavior of a stent surface and has:
a liquid container with a defined liquid, the liquid container and the defined liquid together having a reference weight,
a holding device for holding the stent and moving the stent at least partially in direction of the longitudinal of the stent, which is provided to submerge at least partially the stent in the liquid of the liquid container and
a computer configured to determine a course of a wetting force along a length of the stent surface based on a measured deviation from the reference weight indicative of the wetting force of the stent surface, and configured to determine surface characteristics of the stent surface based on the wetting behavior of the stent surface.

15. Device according to claim 14, wherein the computer detects the wetting force according to a dynamic measurement of the deviation from the reference weight.

16. Device according to claim 14, wherein the device is a dynamic detection device of tensiometric type.

17. Device according to claim 14, wherein the holding device has a linear drive which moves the stent substantially along its longitudinal axis through a liquid surface of the liquid.

18. Device according to claim 14, wherein the device is configured to determine surface characteristics of a stent for implantation in a body lumen based on a wetting behavior of a stent surface, wherein the device is further configured to determine a course of a wetting force along the stent surface for determining the wetting behavior, the wetting force between the stent surface and a liquid surface being detected along the length of the stent.

19. A method for determining uniformity of surface characteristics of the stent surface along the length of the stent and/or purity of the stent surface and/or a change in a hydrophility or hydrophobicity of the stent surface along the length of the stent with a device according to claim 14.

20. Device according to claim 14, further comprising a measuring device that measures the deviation from the reference weight indicative of the wetting force of the stent surface.

* * * * *